United States Patent [19]

Kovacs

[11] Patent Number: 5,011,380
[45] Date of Patent: Apr. 30, 1991

[54] MAGNETICALLY ACTUATED POSITIVE DISPLACEMENT PUMP

[75] Inventor: Steven G. Kovacs, Oldsmar, Fla.

[73] Assignee: University of South Florida, Tampa, Fla.

[21] Appl. No.: 300,361

[22] Filed: Jan. 23, 1989

[51] Int. Cl.$^5$ .............................................. F04B 43/14
[52] U.S. Cl. ...................................... 417/413; 417/417
[58] Field of Search ............... 417/395, 413, 416, 417, 417/418, DIG. 1; 92/96, 103 SD; 600/16, 17; 623/3; 604/153; 310/201, 23, 30; 264/227; 335/299, 230, 234

[56] References Cited

U.S. PATENT DOCUMENTS

| | | |
|---|---|---|
| 3,791,769 | 2/1974 | Kovacs . |
| 3,827,426 | 8/1974 | Page et al. .................. 417/413 X |
| 3,842,440 | 10/1974 | Karlson . |
| 3,874,002 | 4/1975 | Kurpanek . |
| 3,919,722 | 11/1975 | Harmison .................. 623/3 |
| 4,028,572 | 6/1977 | Baltisberger .................. 310/201 |
| 4,163,911 | 8/1979 | Simes et al. . |
| 4,213,207 | 7/1980 | Wilson .................. 623/3 |
| 4,243,899 | 1/1981 | Jaffe .................. 335/229 X |
| 4,259,653 | 3/1981 | MCGonigal .................. 335/230 |
| 4,302,854 | 12/1981 | Runge . |
| 4,306,207 | 12/1981 | Tada et al. .................. 335/230 X |
| 4,383,234 | 5/1983 | Yatsushiro et al. .............. 335/230 X |
| 4,468,177 | 8/1984 | Strimling . |
| 4,482,346 | 11/1984 | Reinicke . |
| 4,487,603 | 12/1984 | Harris . |
| 4,534,714 | 8/1985 | Smith . |
| 4,547,911 | 10/1985 | Strimling .................. 417/413 X |
| 4,557,673 | 12/1985 | Chen et al. .................. 600/16 X |
| 4,578,077 | 3/1986 | Joh .................. 623/3 |
| 4,581,018 | 4/1986 | Jassawalla et al. .................. 604/153 |
| 4,602,180 | 7/1986 | Olson .................. 310/201 |
| 4,621,617 | 11/1986 | Sharma . |
| 4,704,591 | 11/1987 | Hafner .................. 335/230 X |
| 4,731,076 | 3/1988 | Noon et al. .................. 417/413 X |
| 4,786,240 | 11/1988 | Koroly et al. .................. 417/413 |
| 4,835,503 | 5/1989 | Everett .................. 335/230 X |
| 4,859,975 | 8/1989 | Vetsuhara .................. 335/230 |

Primary Examiner—Michael Koczo
Assistant Examiner—Eugene L. Szczecina, Jr.
Attorney, Agent, or Firm—Ratner & Prestia

[57] ABSTRACT

A positive displacement pump is provided which is especially suited to be used as a left ventricle assist device (LVAD). The pump is electromagnetically actuated. An electromagnet produces a pulse which repels a magnet mounted in a diaphragm which forms one wall of a pumping chamber. The pumping chamber thereby constricts and fluid is expelled. The electromagnet has a reverse taper core and core cup magnet which produce a bipolar field effect upon a diaphragm magnet to cause the return of the diaphragm to its starting position, without the application of external power.

17 Claims, 2 Drawing Sheets

MAGNETICALLY ACTUATED POSITIVE DISPLACEMENT PUMP

FIELD OF THE INVENTION

This invention relates to a magnetically actuated positive displacement pump for the controlled pulsatile pumping of liquids, and an electromagnetic actuator therefor. The flow rate of liquid, as well as the shape of the pressure wave developed, is variable.

The pump is efficient due to an efficient electromagnetic actuator developed especially for use in this pump. By shaping the electrical pulse to the electromagnetic actuator one can vary the shape of the pressure wave produced by the pump, as well as the flow rate of fluid produced by the pump. The pulsatile action, shaped pressure wave, relatively small size and high efficiency of the pump make it especially useful as a prosthetic heart, to replace or assist a malfunctioning natural heart, or portion thereof.

BACKGROUND OF THE INVENTION

Generally, the object of a prosthetic heart device is to assist or replace the left ventricle of a human heart. The left ventricle suffers the greatest damage in most heart cases and a replacement or aid therefor is desirable. Such devices are known by the acronym LVAD for Left Ventricle Assist Device.

The concept of providing a prosthetic heart device is not new. Many such devices exist, however, each has problems which remain, to date, unsolved. Most LVAD's fall into three general categories: pneumatic, hydraulic and electromagnetic.

Pneumatic devices use external compressors to produce high-pressure air which powers the device. The device is generally intracorporal, and the pneumatic lines pass through the body wall to connect the prosthetic device with the high-pressure air source. The problems associated with such a pneumatic LVAD include the fact that as the pneumatic lines pass through the body wall, there is a high chance of sepsis or infection since the lines pulse with each "beat" of the LVAD.

Additionally, very high pressure air is required to produce a satisfactory pulse rate and pressure in pneumatic LVADs, causing additional complications such as a high chance of valve failure. Pneumatic systems inherently include time lag as the pressure front travels through the pneumatic line. Finally, the quality of life of a patient dependent upon a pneumatic LVAD is poor because the patient is confined to a bed near the high-pressure air source.

Hydraulic LVAD's have a separate set of problems. Such LVAD's generally consist of a motor and pump blade with the pump blade in direct contact with the blood being pumped. Blood is in contact with many surfaces in the pump. Consequently, the number of blood cells damaged during pumping is high, as is the likelihood of platelet aggregation or clotting. Further, the motor's inertia may cause small twisting movements of the LVAD with each pulse, leading to additional complications or patient discomfort.

Finally, electromagnetic LVAD's have been made in many different configurations. Heretofore, those configurations have generally possessed high power requirements. In some instances, this is due to the fact that the pumping mechanism (diaphragm, etc.) lacks means by which to return to its starting position without the use of external power. Therefore, power must be supplied to move the mechanism in both directions. Power is required to pump the blood and to fill the pump chamber with blood from an auricle. These high power requirements also stem from inefficient conversion of electrical energy to magnetomotive force.

SUMMARY OF THE INVENTION

In the electromagnetic pump of the present invention, problems are overcome by a pump design which is inherently more efficient in conversion of electrical energy to magnetomotive force. This pump includes a means for filling the pump chamber with liquid (e.g. blood) without the application of electrical energy. Thus, electrical energy is required for only one-half of the pump's cycle. Further, it utilizes a minimum of moving parts to wear out, break down, or damage blood cells.

The pump has a pump chamber with a movable diaphragm forming one wall. A magnet is coaxially aligned with and attached to the diaphragm. The pump chamber also has two substantially one-way valves, one for the inflow of fluid and one for the outflow. The pump has an electromagnetic actuator. The actuator produces an electromagnetic pulse which repulses a permanent magnet attached to the diaphragm. The permanent magnet and diaphragm move away from the actuator causing a reduction in volume of the pumping chamber and expulsion of fluid through the outlet valve. When electricity to the actuator is switched off, the diaphragm magnet is attracted to the actuator's ferromagnetic core. This causes the diaphragm to return to its initial position, thus increasing the volume of the pumping chamber causing it to fill with fluid.

Preferably, the efficiency of this pumping action is optimized by specific configurations and choice of materials for various pump elements.

DETAILED DESCRIPTION OF THE PREFERRED EMBODIMENT

Figure 2:
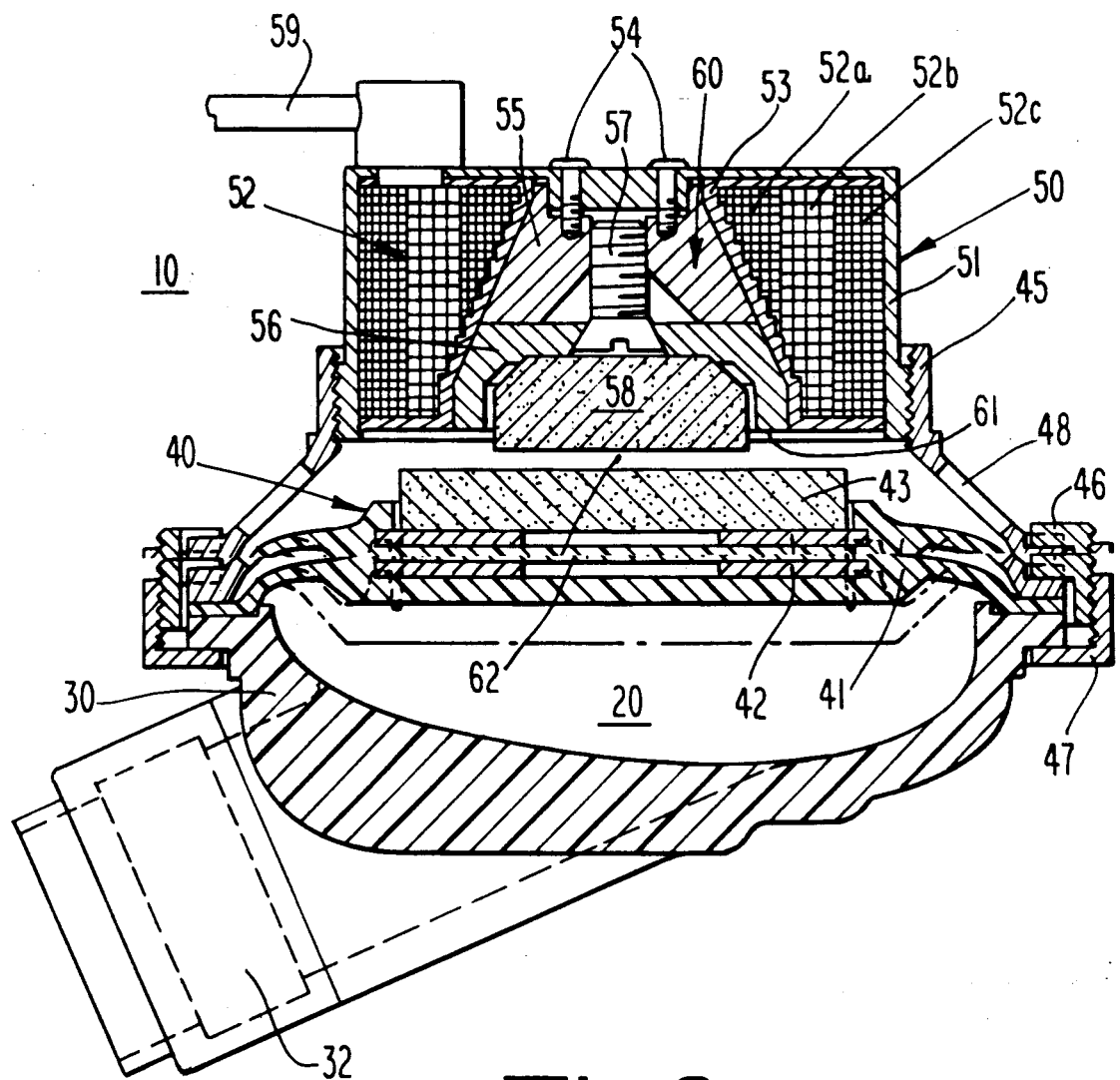
FIG. 2 is a cross sectional view of the pump of the present invention.

Referring now to FIG. 2 there is shown an LVAD 10, including actuator 50 which provides the electromagnetic force to power LVAD 10. Actuator 50 derives power in turn from an external power source via wire leads 59. When implanted in a human body, wire leads 59 may be connected to an extracorporal power source by means of a "skin plug" or some similar apparatus to convey electrical power through the body wall. The particular actuator configuration used in the pump of the present invention solves several problems. First, it is desirable to direct the maximum amount of magnetic flux to front core face 61 and into air gap 62 between front core face 61 and diaphragm magnet 43. Second, it is desirable to provide means whereby diaphragm magnet 43 and diaphragm 41 return to their starting positions without the application of external power. The actuator of the present invention solves both of these problems, as discussed below.

The specific configuration of electromagnetic actuator 50 is important. It includes a ferromagnetic core 60 of three sections: rear core section 55; core cup 56; and core cup magnet 58. Core section 60 is surrounded by bobbin 53 around which are windings 52a, b, and c, collectively referred to as coil 52. The wire used for windings 52a, b and c is preferably rectangular in cross section. Such rectangular wire allows closer packing than wire having a circular cross section. More specifically, rectangular wire allows approximately a 30% decrease in actuator size, because upwards of 95% of the coil volume is occupied by rectangular wire whereas only about a 65% volume efficiency of winding density is achievable with circular wire. Further, uniformity of winding allows close calculation of the magnetic field produced by the coil; therefore the amount of energy required to achieve the desired pumping effect is more easily and closely calculated. Finally, ease of winding is increased with rectangular wire. Such rectangular wire is available upon special order from MWS Wire Industries of West Lake Village, Calif.

The outer surface of bobbin 53 preferably comprises a series of cylindrical sections each of decreasing radius as shown in FIG. 2. This allows for ordered windings of rectangular wire around a tapered core. This is all contained in flux shell 51 and held in place by case screws 54.

Core 60 is a reverse taper hollow core. The front face 61 of core 60 has a greater circumference than the rear face of core 60 (the front face being that face closer to diaphragm assembly 40). This configuration is referred to as a reverse taper core.

The reverse taper core increases magnetic flux density at the front face due to the fact that in such a reverse taper core, the magnetic neutral plane is moved toward that front face. The definition of the magnetic neutral plane is that it is located where all magnetic flux paths will intersect it at right angles.

In a conventional (cylindrical) core, the magnetic neutral plane is coincident with the geometric neutral plane (midpoint between the core ends). By moving this magnetic neutral plane toward front core face 61, the reverse taper core design of this invention allows the core to intercept more of the magnetic flux in the coil region than could be intercepted by a conventional cylindrical core. This allows for lower leakage of the magnetic flux and consequently lower losses in power. Thus, more of the electrical energy input to the coil is converted to magnetic flux at the front core face than would otherwise be possible with a conventional cylindrical core.

Core cup 56 has a hollow central portion in which cup magnet 58 resides. This causes the lines of flux to concentrate in the perimeter of front core face 61. This directs a greater proportion of flux to air gap 62 between core 60 and diaphragm magnet 43. Core cup 56 and rear core section 55 are hollow throughout their entire length. The hollow area is partially filled with non-magnetic core screw 57. This core screw also holds core cup 56 in place. Rear core section 55 and core cup 56 are made from a ferromagnetic material such as Vanadium Permendur. Two sections are necessary only because of the problems involved in machining a single piece of this particular configuration.

Core cup magnet 58 and diaphragm magnet 43 are preferably made of some strong, persistant magnetic material such as neodymium boron iron. This particular material is preferred because it has a high megagauss-oersted (MGO) value. Generally, the MGO value of neodymium boron iron is around 35. Because of this high MGO value, a permanent magnet made from this material will produce a very persistent magnetic field which will not deteriorate significantly with time and high use.

Core cup magnet 58 is held in place by its own magnetic attraction to core cup 56 and rear core section 55. Core cup magnet 58 is centered coaxially in core cup 56 by a small ridge in core cup 56. Core cup magnet 58 is oriented so as to be in a repulsion mode with permanent diaphragm magnet 43.

Core 60 is surrounded by bobbin 53. This bobbin is stepped on its outer surface in order to allow easier and more regular packing of rectangular windings 52a, b, and c than would be possible with a bobbin having smoothly tapered sides. The enhanced magnetic effect of this stepped bobbin and windings is significant in that it allows about a 30% decrease in actuator size. Additionally, ease of winding is greatly increased. This entire arrangement is secured in flux shell 51 by case screws 54. Flux shell 51 is made of any standard ferromagnetic material. Bobbin 53 is made of non-magnetic material such as plastic or ceramic.

Actuator 50 is attached to interface mount 45 by means of threads in the interface mount and on actuator flux shell 51. Actuator 50 is held in place in interface mount 45 by set screws (not shown). Interface mount 45 is held to diaphragm 40 and pump chamber wall 30 by means of upper ring clamp 46 and lower ring clamp 47. Upper ring clamp 46 and lower ring clamp 47 secure to one another by means of threads.

Figure 4:
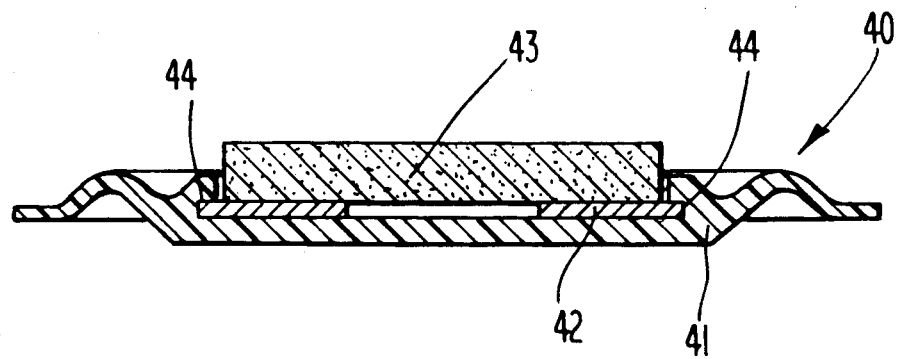
FIG. 4 is a cross sectional view of the diaphragm assembly of the pump of the present invention.

As shown in FIG. 4, diaphragm assembly 40 consists of diaphragm 41, diaphragm magnet 43 and backing plate 42. Backing plate 42 has an annular configuration. The backing plate 42 is held in place in diaphragm 41 by means of a small annular recess into which backing plate 42 fits snugly. Diaphragm magnet 43 is held to backing plate 42 by means of the magnetic attraction between them. Backing plate 42 is made of some standard ferromagnetic material such as Vanadium Permendur. Backing plate 42 helps enhance the flux density through the front and rear planes of pusher plate magnet 43. Preferably, the ratio of the radii of the backing plate to the diaphragm magnet is 1.2:1. Diaphragm 41 has a double roll as can be seen from FIG. 4. From the outside of the diaphragm moving inward, the diaphragm first turns upward, then turns downward below its original level. This double roll allows for greater flexibility of movement of diaphragm 41.

Figure 3:
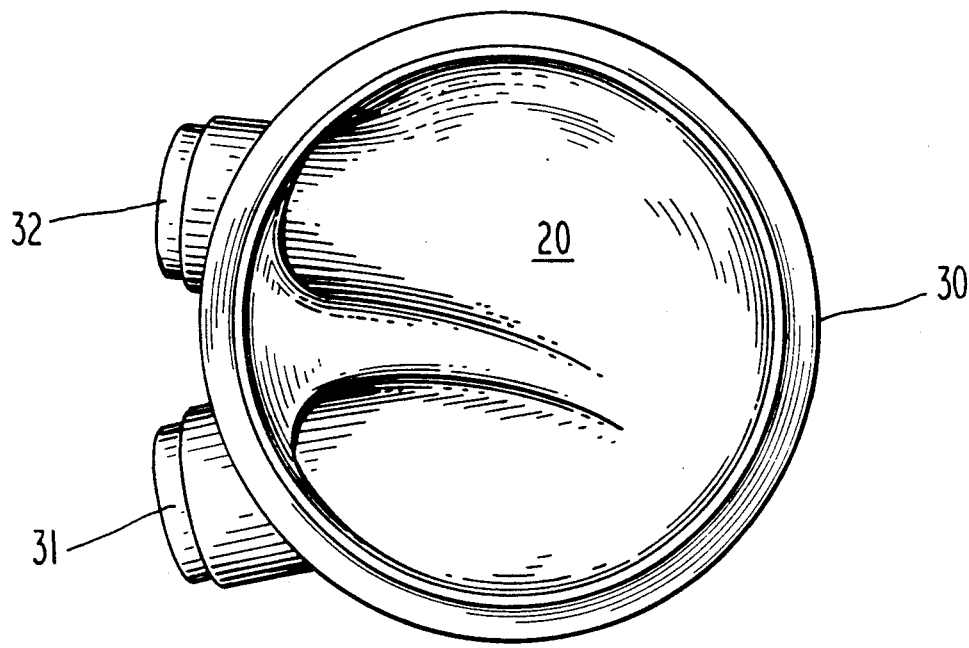
FIG. 3 is a plan view of the inside of the pump chamber wall.

As may be seen in FIG. 2, diaphragm assembly 40 forms one wall of pump chamber 20. The remainder of pump chamber 20 is formed by pump chamber wall 30. Pump chamber wall 30 is also shown in FIG. 3. Pump chamber wall 30 is asymmetrical and has an inlet port 31 and an outlet port 32. The asymmetric shape of pump chamber wall 30 enables increased efficiency for pumping by providing positive vector control for flow movement toward the outlet port region of the pump. Asymmetric pump chamber wall 30 therefore lowers the power requirements of LVAD 10.

Fluid flows in through inlet port 31 as diaphragm 41 moves toward actuator 50. Upon application of pressure by diaphragm 40, fluid is preferentially directed toward outlet port 32 by virtue of chamber asymmetry. Any fluid directed back toward inlet port 31 is prevented from exiting the chamber by a conventional one-way valve (not shown) installed in inlet port 31. A similar valve allowing only the outflow of fluid is installed in outlet port 32. Suitable valve assemblies approved for use in humans are available from a number of manufacturers, including Medtronic, Inc. of Minneapolis, Minn. or St. Jude, also of Minneapolis, Minn. The inlet and outlet valves are preferably of 27 and 25 millimeter lumen respectively.

Pump chamber wall 30 and diaphragm 41 are both made of a suitably inert (with respect to the fluid being pumped), somewhat flexible material. Because of the specific requirements of an LVAD, the preferred material for LVAD 10 (and for other vascular system prosthetic devices as well, such as veins and arteries) is the copolymer of polytetramethylene oxide-di-p-aminobenzoate (hereinafter "aminobenzoate") and diphenylmethane diisocyanate (hereinafter "diisocyanate") available for example from Mobay Chemicals of Delaware. The former is available from several chemical producers including ICI Corp. of New Jersey, Mobay Chemicals of Delaware or Polaroid Corporation of Assonet, Mass. (under the tradename Polamine 1000). By varying the proportions of aminobenzoate and diisocyanate, one can controllably moderate the flexibility of the polymer. For example, in pump chamber wall 30, the polymeric resin includes preferably 7 parts aminobenzoate and 6 parts diisocyanate, with a resulting shore A hardness value of between 85 and 90 once cured. The polymeric resin of diaphragm 41 preferably includes 8.5 parts aminobenzoate and 5.5 parts diisocyanate, with a resulting shore A hardness value of between 55 and 60 once cured. Preferably, diaphragm 41 is more flexible than pumping chamber wall 30, since pumping chamber wall 30 is relatively stationary, while diaphragm 40 oscillates.

Pump chamber wall 30 and diaphragm 41 are preferably pour cast in an RTV (Room Temperature Vulcanizing) silicone mold, the mold itself having been formed using an electropolished acrylic, e.g. polymethyl methylacrylate (Lucite) master. This, (with the preferred casting composition referred to above) provides a smooth surface which minimizes platelet aggregation. Traditional molding methods such as injection molding or vacuum forming give rise to difficulties not experienced when an RTV silicone mold is used. Injection molding leaves inherent stress points and weak spots in the pumping chamber. Vacuum forming results in very small irregularities which can lead to platelet aggregation and blood clot formation.

Because of its peculiarly good resistance to clot formation and platelet aggregation, the particular copolymer heretofore described in conjunction with RTV silicone mold pour casting, may also be used to produce artificial veins and arteries to be used either alone or in conjunction with the LVAD of the present invention.

Such materials and methods lead to a very smooth, inert and controllably flexible product which produces only a minimum of platelet aggregation. This copolymer also possesses longevity, leading to a minimum of complications due to apparatus failure from use. Further, as indicated above, the flexibility of the final product may be controllably moderated by the particular proportions of components used.

One aspect of this invention is the making of vascular system prosthetic devices, such as artificial heart chambers, veins, arteries, etc. by the method just described. The resultant products of this method are also another aspect of this invention. The method comprises, in general, making a prosthetic device for the vascular system by forming a positive acrylic master of the device and surface polishing the master. An RTV silicone negative mold is formed from the master, and the device is pour formed using the mold, by coating the mold with a mixture of aminobenzoate and diisocyanate. The resin is then cured such as by heat curing and removed from the mold. Preferably, the master is made from electropolished polymethyl methylacrylate (Lucite). The preferred polymeric resin is a mixture of polytetramethylene oxide-di-p-aminobenzoate and diphenylmethane diisocyanate (as previously indicated).

In operation, diaphragm 41 is at rest in the position shown in FIG. 2. Pumping chamber 20 is filled with blood. Electrical energy is applied via wire leads 59 to various windings 52a, 52b, and 52c. Each winding is individually actuable. The magnetic force thus generated is channeled through core 60 to repel diaphragm magnet 43. This repulsion causes a movement of diaphragm 41 to the position shown in shadow in FIG. 2. This causes a reduction in volume of pumping chamber 20 and expels blood out through outlet port 32. By correctly shaping the electrical pulses supplied to various windings 52a, b and c, the pulsatile pumping action of LVAD 10 may be made to simulate the pumping action of an actual heart ventricle, producing a pressure wave for an output which is very similar to that produced by a natural heart ventricle.

At this point, the electrical power is switched off. Permanent diaphragm magnet 43 is attracted to the non-magnetized ferromagnetic material in core 60 as well as the ferromagnetic material of flux shell 51. However, core cup magnet 58 is in a repulsion mode with diaphragm magnet 43. The attraction between diaphragm magnet 43 and the ferromagnetic material in actuator 50 is stronger than the repulsion created by core cup magnet 58. Diaphragm 41 begins to move toward actuator 50, increasing the volume of pump chamber 20 and drawing blood in through inlet port 31. The movement of diaphragm 41 toward actuator 50 is slowed by the increase in repulsion between core cup magnet 58 and diaphragm magnet 43.

This bipolar field effect (both attraction and repulsion being present at the same time) slows the movement of diaphragm 41 toward actuator 50. If this movement were too rapid, an undue strain would be placed upon the auricle from which blood is drawn through inlet port 31. This bipolar field effect also prevents a large magnetic attraction from building up between diaphragm magnet 43 and the ferromagnetic portions of actuator 50. Such a high magnetic attraction would be difficult to overcome for each succeeding pump cycle, and the pump operation would require large amounts of power. Instead, the power needed to repulse diaphragm magnet 43 and pump blood out of outlet port 32 is kept to a minimum, as are the power requirements of the overall operation of the LVAD.

At rest, diaphragm 41 is fully extended toward actuator 50. An air gap 62 occurs between pusher plate magnet 43 and core cup magnet 58. The width of this air gap may be adjusted since, as previously explained, the actuator is held by threads into interface mount 45.

Figure 1:
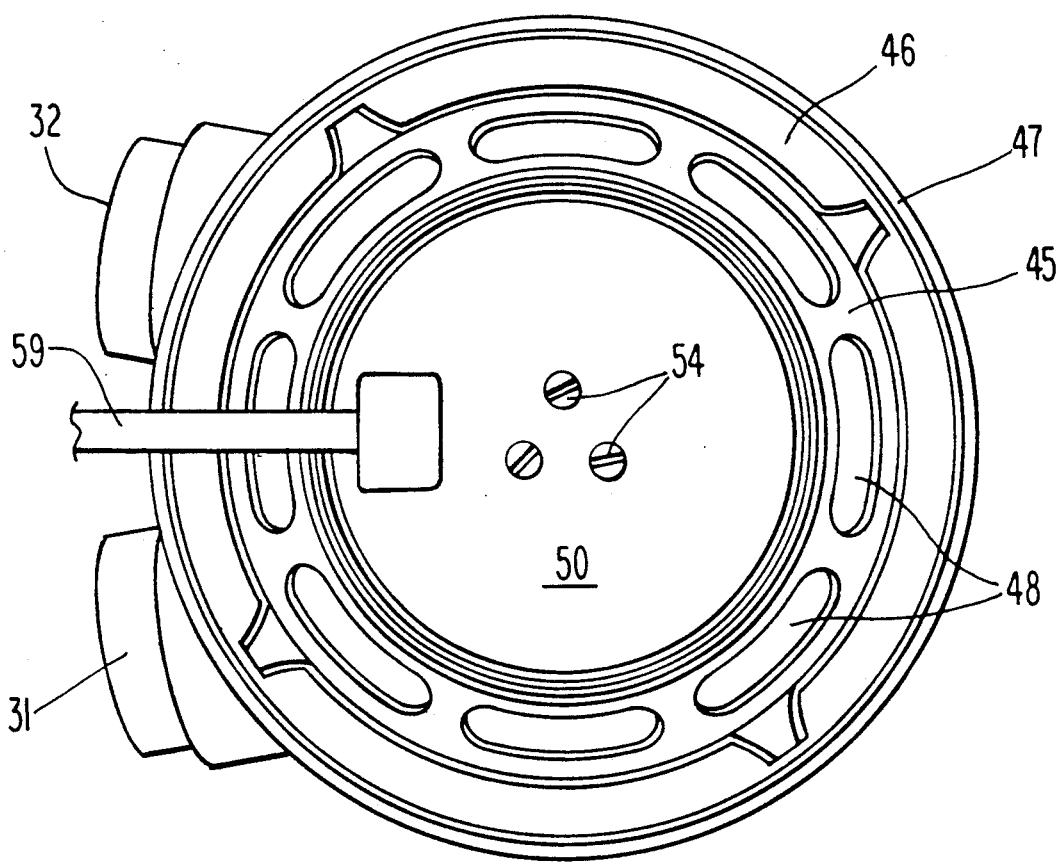
FIG. 1 is a plan view of the pump of the present invention.

As shown in FIGS. 1 and 2, interface mount 45 is equipped with interface mount ports 48. These ports allow air to flow freely in and out from between pusher plate magnet 43 and core cup magnet 58. When used as an LVAD, this air is supplied from an area surrounding the actuator and enclosed by an outer bag or jacket.

What is claimed is:

1. An apparatus for the pulsatile pumping of liquids comprising:
    a pumping chamber having inlet and outlet valves, wherein one wall of said chamber comprises a flexible diaphragm, said diaphragm having a permanent magnet centrally disposed therein in coaxial alignment therewith;
    electromagnetic means for repulsing said permanent diaphragm magnet from a starting position when current is supplied to said electromagnetic means; and
    magnetic means for returning said diaphragm to its starting position when said current is interrupted.

2. The apparatus of claim 1, wherein said chamber, diaphragm, permanent magnet and electromagnet have circular cross-sections and are coaxially aligned.

3. The pump of claim 1 wherein said bias force means is a permanent magnet attached to said diaphragm and attracted to said electromagnet upon deactivation of said electromagnet.

4. The pump of claim 3 wherein the chamber configuration, period of intermittency with which said electromagnet is activated, and configuration and strength of said electromagnet and said permanent magnet are selected, in combination, to produce upon said reciprocal operation of said diaphragm, a pulse action simulating that of a natural heart.

5. An apparatus for simulating the pumping action of a ventricle of a heart comprising;
    a pumping chamber including substantially unidirectional inlet and outlet valves, and a flexible diaphragm having a magnet attached thereto and coaxially aligned therewith, said diaphragm magnet being a permanent magnet;
    electromagnetic means for repulsing said permanent diaphragm magnet from a starting position when current is supplied to said electromagnetic means; and
    magnetic means for returning said diaphragm to its starting position when said current is interrupted.

6. An apparatus for simulating the pumping action of a ventricle of a heart comprising;
    a pumping chamber including substantially unidirectional inlet and outlet valves, and a flexible diaphragm having a magnet attached thereto and coaxially aligned therewith, said diaphragm magnet being a permanent magnet; and
    a second magnet, coaxially aligned with said diaphragm magnet, said second magnet comprising a core and windings;
    said core comprising;
    a conically-shaped rear core section,
    a cup-shaped front core section;
    said diaphragm magnet being attracted to said core when said windings are not energized and repulsed by said core when said windings are energized.

7. The apparatus of claim 6 wherein said windings comprise wire having a non-circular cross section.

8. The apparatus of claim 6 further comprising
    a permanent cup magnet positioned to magnetically repulse said diaphragm magnet, said cup magnet located within said front core section;
    wherein all of said diaphragm, diaphragm magnet, front core section, rear core section and permanent cup magnet are all in coaxial alignment.

9. The apparatus of claim 8 wherein
    when an appropriate pulse of electrical energy is applied to said windings, a net repulsive force is created between said core and said diaphragm magnet, forcing said diaphragm away from said core and decreasing the volume of said pumping chamber, producing a varying pressure in said chamber simulating the varying pressure in a heart ventricle.

10. A pump comprising a pumping chamber including a movable diaphragm and a stationary rigid pumping chamber wall, said chamber wall having substantially unidirectional inlet and outlet valves, said chamber wall being asymmetrical such that fluid contained in said pumping chamber preferentially flows toward said outlet valve upon a rise in fluid pressure within said pumping chamber due to movement of said diaphragm.

11. The pump of claim 10 adapted to simulate the pumping action of a ventricle of a human heart.

12. A ventricular assist device powered by an electromagnet, including a core and windings, and a mating permanent magnet, said permanent magnet, core, windings and electromagnet being coaxially aligned, said electromagnet and permanent magnet positioned to be attracted to and repulsed by one another, along a line coaxial with said electromagnet and permanent magnet upon activation and deactivation of said electromagnet,
    said ventricular assist device further comprising a pump chamber having a moveable diaphragm and a fixed pump chamber wall, said permanent magnet being mounted to said moveable diaphragm, and said chamber wall having an asymmetric configuration such that when said permanent magnet is repulsed by said electromagnet, the volume of said pump chamber decreases and fluid therein is preferentially directed to an outlet port in said pump chamber wall.

13. The device of claim 12 wherein said pump chamber and diaphragm have a smooth surface resulting from pour casting said diaphragm and pump chamber wall in an RTV silicone mold.

14. The device of claim 13 wherein said pump chamber wall and diaphragm comprise copolymers of polytetramethylene oxide-di-p-aminobenzoate and diphenylmethane diisocyanate.

15. A pump having a moveable diaphragm reciprocally activated by an electromagnet including means to activate said electromagnet intermittently, and upon said electromagnet activation, to produce an electromagnetic force causing said diaphragm to move away from said electromagnet, said pump including means for producing a bias force tending to move said diaphragm toward said electromagnet wherein said diaphragm comprises one wall of a pump chamber which includes a pump chamber wall, said pump chamber wall having an asymmetrical configuration such that upon activation of said electromagnet, and a rise in pressure of fluid contained in said pump chamber, said fluid is preferentially directed toward an outlet port in said pump chamber wall.

16. The pump of claim 15 wherein the chamber configuration, period of intermittency with which said electromagnet is activated, and configuration and strength of said electromagnet and said permanent magnet are selected, in combination, to produce upon said reciprocal operation of said diaphragm, a pulse action simulating that of a natural heart.

17. An apparatus for the pulsatile pumping of liquids comprising:
- a pumping chamber having inlet and outlet valves, wherein one wall of said chamber comprises a flexible diaphragm, said diaphragm having a permanent magnet centrally disposed therein; and
- an electromagnet aligned such that when current is supplied to said electromagnet, a repulsive force is generated between said electromagnet and said diaphragm magnet, and when no current is supplied to said electromagnet, an attractive force exists between said electromagnet and said diaphragm magnet;
- said electromagnet comprising a ferromagnetic core and coil, said core comprising a truncated cone-shaped rear core section, cup-shaped front core section, and a cup magnet,
- said cup magnet being a permanent magnet and aligned such that a repulsive force exists between said cup magnet and said diaphragm magnet;
- said chamber, diaphragm, permanent magnet, electromagnet, cup magnet, rear core section, and front core section being coaxially aligned.

* * * * *